United States Patent
Barnes et al.

(10) Patent No.: US 6,626,170 B1
(45) Date of Patent: Sep. 30, 2003

(54) DRUG DELIVERY DEVICES

(75) Inventors: Paul Barnes, King's Lynn (GB); Marc Lechner, King's Lynn (GB); Richard John Warby, Wisbech (GB)

(73) Assignee: Bespak PLC, Norfolk (GB)

( * ) Notice: Subject to any disclaimer, the term of this patent is extended or adjusted under 35 U.S.C. 154(b) by 0 days.

(21) Appl. No.: 09/763,177

(22) PCT Filed: Jun. 22, 1999

(86) PCT No.: PCT/GB99/01961
§ 371 (c)(1),
(2), (4) Date: Feb. 20, 2001

(87) PCT Pub. No.: WO00/12163
PCT Pub. Date: Mar. 9, 2000

(30) Foreign Application Priority Data

Aug. 26, 1998 (GB) ............................................... 9818644

(51) Int. Cl.[7] ............................................. A61M 11/00
(52) U.S. Cl. ............................. 128/200.23; 128/205.24
(58) Field of Search ...................... 128/200.11, 200.12, 128/200.14, 200.23, 203.12, 203.14, 203.15, 203.21, 205.24; 428/521; 137/907, 908

(56) References Cited

U.S. PATENT DOCUMENTS

| 3,342,754 | A | * | 9/1967 | Gorham ..................... 528/396 |
| 3,379,803 | A | * | 4/1968 | Tittmann et al. .............. 264/81 |
| 4,225,647 | A | * | 9/1980 | Parent ....................... 428/336 |
| 4,808,453 | A | | 2/1989 | Romberg et al. |
| 4,882,210 | A | * | 11/1989 | Romberg et al. .......... 428/34.7 |
| 4,973,504 | A | | 11/1990 | Romberg et al. |
| 5,000,994 | A | | 3/1991 | Romberg et al. |
| 5,064,083 | A | * | 11/1991 | Alexander et al. .......... 215/247 |
| 5,354,286 | A | * | 10/1994 | Mesa et al. .................. 604/218 |
| 5,490,497 | A | * | 2/1996 | Chippendale et al. .. 128/200.14 |
| 5,576,068 | A | * | 11/1996 | Caburet et al. ............. 427/452 |
| 5,642,727 | A | * | 7/1997 | Datta et al. ............ 128/202.25 |
| 5,836,299 | A | * | 11/1998 | Kwon .................... 128/200.14 |
| 5,871,010 | A | * | 2/1999 | Datta et al. ............ 128/203.12 |
| 5,875,776 | A | * | 3/1999 | Vaghefi ................. 128/203.12 |
| 6,036,942 | A | * | 3/2000 | Alband .................. 128/200.23 |
| 6,112,950 | A | * | 9/2000 | Di Giovanni et al. ... 222/402.1 |
| 6,122,950 | A | * | 9/2000 | Rosenthal et al. ............. 72/200 |
| 6,143,277 | A | * | 11/2000 | Ashurst et al. ........ 128/203.15 |
| 6,253,762 | B1 | * | 7/2001 | Britto .................... 128/200.14 |

FOREIGN PATENT DOCUMENTS

| FR | 2 740 527 | 4/1997 |
| FR | 2 756 502 | 6/1998 |
| WO | WO 95 15777 | 6/1995 |

OTHER PUBLICATIONS

"Parylene Conformal Coatings Specifications and Properties", SCS Specialty Coating Systems, Copyright 8/94.*
http://www.scscookson.com/application/medical.htm; "Parylene Coating" Cookson Electronics Equipment.*

* cited by examiner

Primary Examiner—T K Mitchell
(74) Attorney, Agent, or Firm—Smith, Gambrell & Russell, LLP

(57) ABSTRACT

The invention relates to improvements to drugs delivery devices, in particular, those for dispensing a metered dose of medicament. There is provided apparatus (10, 110) for dispensing a medicament wherein at least a portion of one or more of the surfaces of components of the apparatus which come into contact with the medicament during storage or dispensing has a layer of a poly-para-xylylene polymer also known as parylene bonded to at least a portion thereof.

12 Claims, 2 Drawing Sheets

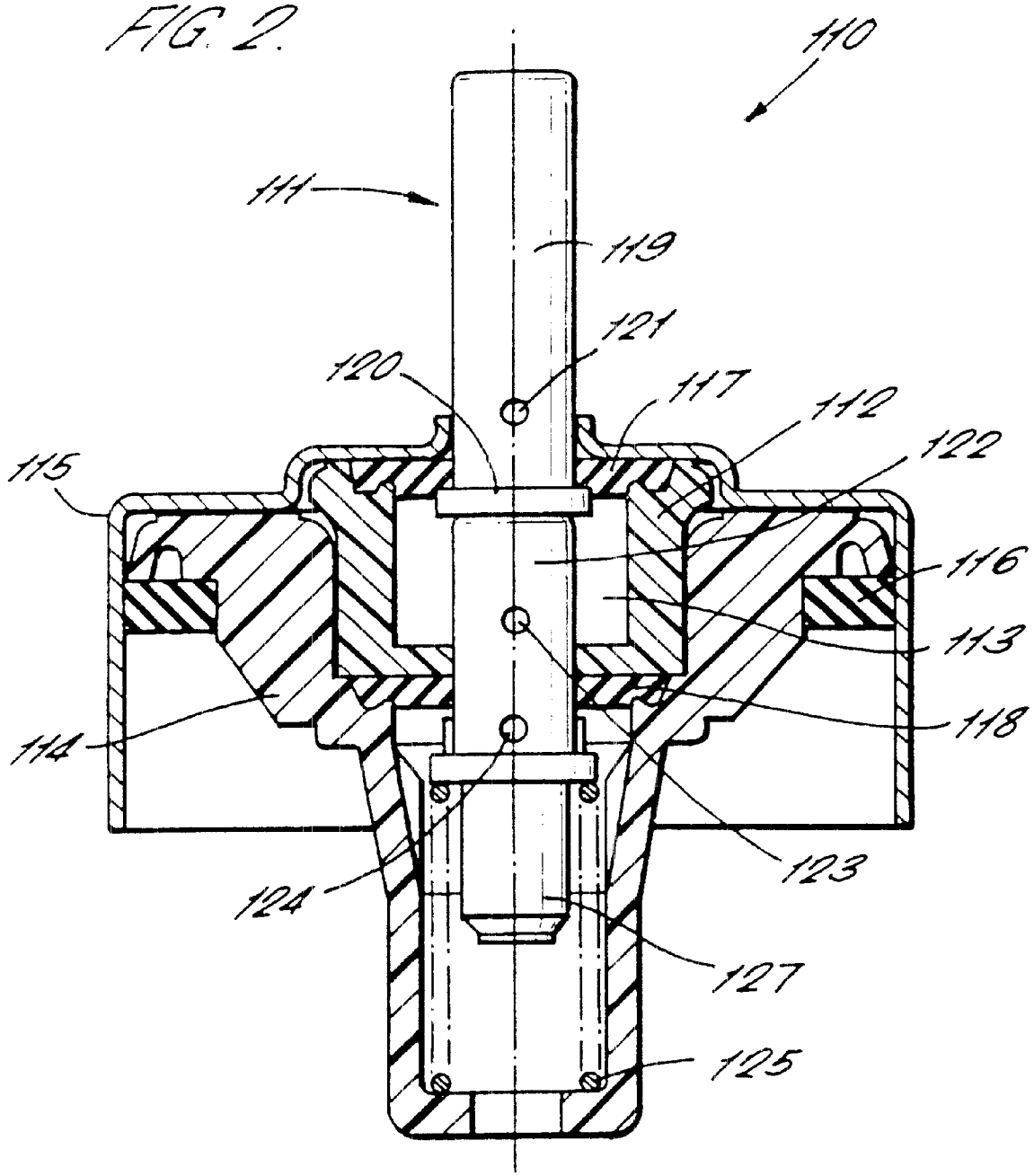

DRUG DELIVERY DEVICES

BACKGROUND OF THE INVENTION

This invention relates to improvements in drug delivery devices and particularly those for dispensing a metered dose of a medicament.

In metered dose inhalers, an aerosol stream from a pressurised dispensing container is fired towards a patient or user of the inhaler into an air flow. The air flow is created by a user inhaling through a mouthpiece of the inhaler and the medicament is released into this air flow at a point between the air inlet holes and the mouthpiece.

Conventional metering valves for use with pressurised dispensing containers comprise a valve stem coaxially slidable within a valve member defining an annular metering chamber, and outer and inner annular seals operative between the respective outer and inner ends of the valve stem and the valve member to seal the metering chamber therebetween. The valve stem is hollow whereby in a non-dispensing position of the valve stem, the metering chamber is connected to the container and charged with product therefrom. The valve stem is movable against the action of a spring to a dispensing position wherein the metering chamber is isolated from the container and vented to atmosphere for the discharge of product.

Other drug delivery devices include apparatus in which capsules containing a powdered medicament are mechanically opened at a dispensing station where inhaled air subsequently entrains the powder, which is then dispensed through a mouthpiece.

A problem with all such drug delivery devices is that deposition of the medicament, or a solid component from a suspension of a particulate product in a liquid propellant, on the internal surfaces and other components of the devices occurs after a number of operation cycles and/or storage. This can lead to reduced efficiency of operation of the device and of the resulting treatment in that deposition of the product reduces the amount of active drug available to be dispensed.

Some prior art devices rely on the dispenser being shaken in an attempt to dislodge the deposited particles as a result of the movement of a liquid propellant and product mixture. However, whilst this remedy is effective within the body of the container itself, it is not effective for particles deposited on the inner surfaces of the metering chamber. As the size of the chamber is significantly smaller, the restricted flow of fluid in the metering chamber (caused by the tortuosity of the flow path through the chamber) means that the fluid in the metering chamber does not move with enough energy to adequately remove the deposited particles.

One solution is proposed in our pending application GB 9721684.0 in which a liner of a material such as fluoropolymer, ceramic or glass is included to line a portion of the wall of a metering chamber in a metering valve. Although this solves the problem of deposition in these types of dispensers, it does require the re-design or modification of mouldings and mould tools for producing the valve members to allow for the insertion of the liner.

FR 2 756 502 describes an aerosol container wherein a paralene coating is applied to the spray pattern block. WO 95/15777 describes an injection device having container having a coating of polyparaxylelene on its inner surface. FR 2 740 527 describes a metering valve common in the art.

BRIEF SUMMARY OF THE INVENTION

It is an object of the present invention to provide drug delivery devices in general in which the deposition of the product and active drug component is minimised.

According to the invention there is provided apparatus for dispensing a medicament comprising a housing adapted to receive a container or capsule for storing the medicament, a mouthpiece and duct means connecting an outlet of the container or capsule with the mouthpiece, characterised in that at least a portion of one or more of the internal surfaces of the duct and/or mouthpiece has a layer of a poly-para-xylylene polymer also known as Parylyne bonded thereto so as to reduce deposition of the medicament on said surfaces.

A particular embodiment of the present invention will now be described, by way of example only, with reference to the accompanying drawings in which:

BRIEF DESCRIPTION OF THE DRAWINGS

FIG. 2 is a cross-sectional view of a metering valve used in another type of drug delivery device.

DETAILED DESCRIPTION OF THE INVENTION

Figure 1:
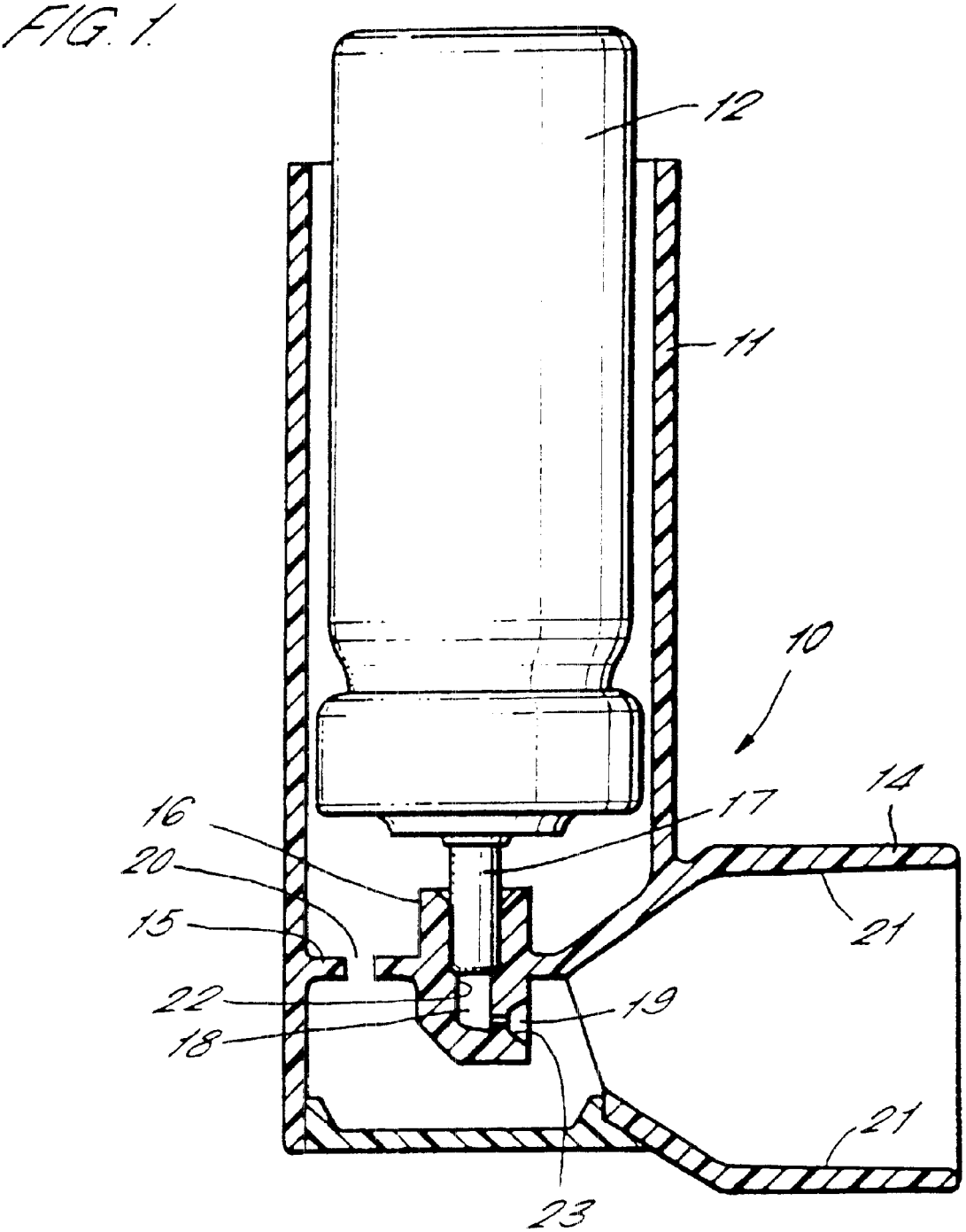
FIG. 1 is a cross-sectional view through an inhaler, which is one type of drug delivery device of the present invention.

In FIG. 1 an inhaler 10 for a product such as a medicament comprises a housing 11 for receiving a pressurised dispensing container 12 of a medicament and a mouthpiece 14 for insertion into the mouth of a user of the inhaler 10.

The container housing 11 is generally cylindrical and open at its upper end. A lower wall 15 of the housing 11 includes an annular socket 16 for receiving the tubular valve stem 17 of the container 12. The socket 16 communicates via a duct 18 ending in an orifice 19 with the mouthpiece 14. The lower wall 15 also has holes 20 for allowing air to flow through the container housing 11 into the mouthpiece 14.

The mouthpiece 14 may be generally circular or shaped to fit the mouth and is connected to or forms a part of the housing 11.

In use, a patient or user holds the inhaler 10, usually in one hand, and applies his mouth to the mouthpiece 14. The user then inhales through the mouthpiece 14 and this creates an airflow through the cylindrical housing 11, from its open end around the dispensing container 12, through the holes 20 and into the mouthpiece 14. After the user has started inhaling through the mouthpiece 14, the container 12 is depressed downwardly onto its stem 17 to release a dose of medicament from the container 12. The dose of medicament is projected by the pressure in the container 12 via the duct 18 and through the orifice 19. It then mixes with the airflow through the mouthpiece 14 and is hence inhaled by the user.

In traditional inhalers, all of the components are plastic mouldings, which gives rise to the deposition problems described above. The particular problem areas in devices such as inhalers are the internal surfaces 21 of the mouthpiece 14, the internal surfaces 22 of the duct 18 and the walls 23 defining the orifice 19. In some inhalers 10, the diameter of at least a part of the duct 18 can be as little as 0.5 mm and so any deposition on its internal surfaces 22 could lead to not only the problem of a reduction in active drug components being available, but also dispensing difficulties.

The metering valve 110 illustrated in FIG. 2 is another type of drug delivery device or dispenser, and includes a valve stem 111 which protrudes from and is axially slidable within a valve member 112, the valve member 112 and valve stem 111 defining therebetween an annular metering chamber 113. The valve member 112 is located within a valve body 114 which is positioned in a pressurised container (not shown) containing a product to be dispensed. The metering valve 110 is held in position with respect to the container by means of a ferrule 115 crimped to the top of the container and sealing being provided between the valve body 114 and container by an annular gasket 116.

An outer seal 117 and an inner seal 118 of an elastomeric material extend radially between the valve stem 111 and the valve member 112. The outer seal 117 is radially compressed between the valve member 112 and valve stem 111 so as to provide positive sealing contact, the compression being achieved by using a seal which provides an interference fit on the valve stem 111 and/or by the crimping of the ferrule 115 onto the pressurised container during assembly.

The valve stem 111 has an end 119 which protrudes from the valve member 112 and ferrule 115 which is a hollow tube and which is closed off by flange 120 which is located within the metering chamber 113. The hollow end 119 of valve stem 111 includes a discharge port 121 extending radially through the side wall of the valve stem 111. The valve stem 111 further has an intermediate section 122, which is also hollow and defining a central passage and which has a pair of spaced radial ports 123, 124 which are interconnected through a central cavity.

A spring 125 extends between a second flange separating the intermediate section 122 of the valve stem 111 and an inner end 127 of the valve stem 111, and an end of the valve body 114 to bias the valve seem 111 in a non-dispensing position in which the first flange 120 is held in sealing contact with the outer seal 117. The second flange is located outside the valve member 112, but within the valve body 114.

The metering chamber 113 is sealed from the atmosphere be the outer seal 117, and from the pressurised container to which the valve 110 is attached by the inner seal 118. In the illustration of the valve 110 shown in FIG. 2 radial ports 123, 124 together with the central cavity in the intermediate section 122 of the valve member 111 connect the metering chamber 113 with the container so that in this non-dispensing condition the metering member 113 will be charged with product to be dispensed.

Upon depression of the valve stem ill relative to the valve member 112 so that it moves inwardly into the container, the radial port 123 is closed off as it passes through the inner seal 118, thereby isolating the metering chamber 113 from the contents of the pressurised container. Upon further movement of the valve stem 111 in the same direction to a dispensing position the discharge port 121 passes through the outer seal 117 into communication with the metering chamber 113. In this dispensing position the product in the metering chamber 113 is free to be discharged to the atmosphere via the discharge port 121 and the cavity in the hollow end 119 of the valve stem 111.

When the valve stem 111 is released, the biasing of the return spring 125 causes the valve stem 111 to return to its original position. As a result the metering chamber 113 becomes recharged in readiness for further dispensing operations.

The component parts of conventional drug dispensing devices, such as valve members, valve stems, inhaler housings and so on, are generally formed as single mouldings from material such as acetal, polyester or nylon which are prone to the deposition problems described above. Although in some cases it might be possible to include a separate liner of a material such as a fluoropolymer, ceramic or glass to line a portion of the area in which deposition problems occurs, this requires the re-design or modification of mouldings and mould tools so that the components can accommodate such lines.

In the present invention we propose a solution in which the component parts of the drug dispensing devices are made by conventional tooling and moulds from the traditional materials listed above. They are then coated with a thin layer of a polymer from the poly-para-xylylene family, also known as the Parylene family, preferably using a Vapour Deposition Polymerisation (VDP) technique. Whilst the poly-para-xylylene polymer may be applied by spray coating or dipping, VDP has the advantage that the poly-para-xylylene coating is formed spontaneously on the component parts at or near room temperatures. Thus thermoplastic materials such as polybutyrene terephthalate (PBT), nylon, acetal and tetrabutyrene terephthalate (TBT) can be treated without fear of thermal damage.

It has been found that coating the surface of component parts with Parylene significantly reduces the deposition of active drugs on the relevant surfaces due to factors such as high conformity, absence of pinholes and coefficients of static and dynamic friction between 0.25 and 0.35 giving good friction reduction. Parylene exists in three variants, commonly referred to as Parylene N, Parylene C and Parylene D, as shown below.

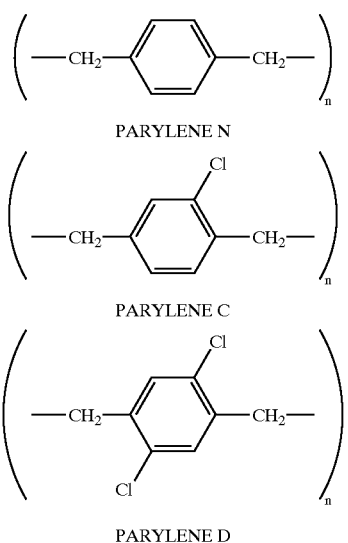

PARYLENE N

PARYLENE C

PARYLENE D

Parylene N has been found to exhibit the best anti-frictional properties (coefficient of static friction 0.25, coefficient of dynamic friction 0.25) and is thus preferred in use over Parylene C and D where low friction is important.

Either an entire component within the drug delivery device, or just the surfaces of one or more component which would come into contact with the medicament during actuation, could be treated to provide an improved drug delivery device according to the present invention. In the case of the type of inhalers as shown in FIG. 1, surfaces 21, 22 and 23 may be treated. In a typical dry powder inhaler, the inner surface of the mouthpiece and any channel leading to the mouthpiece from the point of powder storage, i.e. from a capsule, bulk storage chamber or a pre-metered chamber of a device. In the metering valve of FIG. 2, the valve member 112 alone may be treated. However additional benefits can be achieved in treating some or all of the other plastic and rubber parts of the valve, including, for example, the valve body 114 and the seals 116, 117 and 118. In addition, the metal parts exposed to the drug formulation may also be treated, for example, the dispensing container 12, the spring 125 or the ferrule 115. The method can also be used to treat components of many other delivery devices including nasal pumps, non-pressurised actuators, foil storage types, breath actuated inhaler devices and breath co-ordinating devices and so on.

What is claimed is:

1. Apparatus for dispensing medicament, wherein the apparatus is a metering valve for use with a pressurised dispensing container, the valve comprising a valve stem co-axially slidable within a valve member, said valve member and valve stem defining an annular metering chamber, outer and inner annular seals operative between respective outer and inner ends of the valve member and the valve stem to seal the annular metering chamber therebetween, wherein at least a portion of the metering valve has a layer of poly-para-xylylene polymer bonded to at least a portion of one or more internal surfaces of the metering chamber, so as to reduce deposition of medicament on said surfaces, and wherein said one or more internal surfaces are coated with the poly-para-xylylene polymer by vapor deposition polymerization at or near room temperature to form a vapor deposition bonded layer of poly-para-xylylene polymer.

2. Apparatus as claimed in claim 1, in which at least a portion of a surface of the valve member has the layer of poly-para-xylylene polymer bonded thereto.

3. Apparatus as claimed in claim 1, in which at least a portion of a surface of the valve stem or inner end has the layer of poly-para-xylylene polymer bonded thereto.

4. Apparatus as claimed in claim 1, in which at least a portion of a surface of said seal has the layer of poly-para-xylylene polymer bonded thereto.

5. Apparatus as claimed in claim 1, in which the valve further comprises a valve body in which the valve member is located, the valve body having the layer of poly-para-xylylene polymer bonded to at least a portion of its surface.

6. Apparatus as claimed in claim 1, further comprising a gasket extending between sealing surfaces of said seals of the metering valve and a pressurised dispensing container, said gasket having the layer of poly-para-xylylene polymer bonded to at least a portion of a surface of said gasket.

7. Apparatus as claimed in claim 1, wherein the polymer is one of Parylene C, Parylene N or Parylene D.

8. Apparatus as claimed in claim 1, in which the treated portion is made from a plastic polymer or synthetic rubber.

9. Apparatus as claimed in claim 1, in which the treated portion is made from a metal or alloy.

10. Apparatus as recited in claim 1 wherein said valve comprises a surface of synthetic rubber material on which is bonded the vapor deposition bonded layer of poly-para-xylylene polymer.

11. Apparatus as recited in claim 1 wherein said valve includes a surface of thermoplastic material on which is bonded the vapor deposition bonded layer of poly-para-xylylene polymer.

12. Apparatus recited in claim 1 wherein said valve includes rubber material on which is provided the vapor deposition bonded layer of poly-para-xylylene polymer.

* * * * *